(12) United States Patent
Sappey et al.

(10) Patent No.: US 7,729,566 B2
(45) Date of Patent: Jun. 1, 2010

(54) METHOD FOR THE MONITORING AND CONTROL OF A PROCESS

(75) Inventors: Andrew D. Sappey, Lakewood, CO (US); James Howell, Louisville, CO (US); Henrik Hofvander, Boulder, CO (US); Bernard Patrick Masterson, Boulder, CO (US)

(73) Assignee: Zolo Technologies, Inc., Boulder, CO (US)

( * ) Notice: Subject to any disclaimer, the term of this patent is extended or adjusted under 35 U.S.C. 154(b) by 65 days.

(21) Appl. No.: 11/782,475

(22) Filed: Jul. 24, 2007

(65) Prior Publication Data

US 2008/0074645 A1 Mar. 27, 2008

Related U.S. Application Data

(63) Continuation of application No. 10/543,288, filed as application No. PCT/US2004/010048 on Mar. 31, 2004, now Pat. No. 7,248,755.

(60) Provisional application No. 60/459,108, filed on Mar. 31, 2003.

(51) Int. Cl.
*G02B 6/00* (2006.01)
(52) U.S. Cl. .............................. 385/13; 356/51; 356/73; 385/37
(58) Field of Classification Search .................. 385/13, 385/37; 356/51, 73
See application file for complete search history.

(56) References Cited

U.S. PATENT DOCUMENTS 4,360,372 A 11/1982 Maciejko (Continued)

FOREIGN PATENT DOCUMENTS

CN 1343873 4/2002

(Continued)

OTHER PUBLICATIONS

Allen (1998) "Diode laser absorption sensors for gas-dynamic and combustion flows" Measuring Science and Technology 9:545.

(Continued)

*Primary Examiner*—Ellen Kim
(74) *Attorney, Agent, or Firm*—Swanson & Bratschun, L.L.C.

(57) ABSTRACT

A method of sensing a process utilizing a sensing apparatus consisting of more than one diode laser having select lasing frequencies, a multiplexer optically coupled to the outputs of the diode lasers with the multiplexer being further optically coupled to a pitch side optical fiber. Multiplexed laser light is transmitted through the pitch side optical fiber to a pitch optic operatively associated with a process chamber which may be a combustion chamber or the boiler of a coal or gas fired power plant. The pitch optic is oriented to project multiplexed laser output through the process chamber. Also operatively oriented with the process chamber is a catch optic in optical communication with the pitch optic to receive the multiplexed laser output projected through the process chamber. The catch optic is optically coupled to an optical fiber which transmits the multiplexed laser output to a demultiplexer. The demultiplexer demultiplexes the laser light and optically couples the select lasing frequencies of light to a detector with the detector being sensitive to one of the select lasing frequencies.

19 Claims, 6 Drawing Sheets

U.S. PATENT DOCUMENTS

| | | | |
|---|---|---|---|
| 4,895,421 | A | 1/1990 | Kim et al. |
| 4,915,468 | A | 4/1990 | Kim et al. |
| 4,989,979 | A | 2/1991 | Buckman |
| 5,042,905 | A | 8/1991 | Anjan et al. |
| 5,396,506 | A | 3/1995 | Ball |
| 5,448,071 | A | 9/1995 | McCaul et al. |
| 5,477,323 | A | 12/1995 | Andrews et al. |
| 5,506,721 | A | 4/1996 | Hikami et al. |
| 5,621,213 | A | 4/1997 | Barshad |
| 5,798,840 | A | 8/1998 | Beiting |
| 5,802,222 | A | 9/1998 | Rasch et al. |
| 5,813,767 | A | 9/1998 | Calabro et al. |
| 5,960,129 | A | 9/1999 | Kleinschmitt |
| 6,016,372 | A | 1/2000 | Fein et al. |
| 6,150,661 | A | 11/2000 | McCaul et al. |
| 6,160,255 | A | 12/2000 | Sausa |
| 6,169,830 | B1 | 1/2001 | Kewitsch |
| 6,345,134 | B1 | 2/2002 | Laming et al. |
| 6,363,190 | B1 | 3/2002 | Chen |
| 6,455,851 | B1 | 9/2002 | Lord et al. |
| 6,519,385 | B1 | 2/2003 | Green |
| 6,593,573 | B1 | 7/2003 | McCann et al. |
| 6,766,070 | B2 | 7/2004 | Williams et al. |
| 6,791,689 | B1 | 9/2004 | Weckstrom |
| 2002/0031737 | A1* | 3/2002 | Von Drasek et al. ......... 431/79 |
| 2002/0158202 | A1* | 10/2002 | Webber et al. ......... 250/339.13 |
| 2002/0181856 | A1 | 12/2002 | Sappey et al. |
| 2003/0026541 | A1* | 2/2003 | Sappey et al. ................. 385/37 |
| 2004/0101305 | A1* | 5/2004 | Jung et al. .................... 398/71 |
| 2008/0002186 | A1* | 1/2008 | Masterson et al. ......... 356/73.1 |

FOREIGN PATENT DOCUMENTS

| | | |
|---|---|---|
| EP | 766080 | 2/1997 |
| JP | 409152126 A * | 6/1997 |
| JP | 2000-074830 | 3/2000 |

OTHER PUBLICATIONS

Allen et al. (2002) Tunable Diode Laser Sensing and Combustion Control in *Applied Combustion Diagnostics*, chapter 18.

Baer, et al. (1994) "Multiplexed Diode-Laser Sensor System for Simultaneous H20, 02, and Temperature Measurements" Optics Letters vol. 19, No. 22, pp. 1900-1902, Nov. 15, 1994.

Docquier and Candel (2002) "Combustion control and sensors: a review" Progress in Energy and Combustion Science 28, 107-150.

Ebert et al. (1998) "Simultaneous Laser-Based in situ Detection of Oxygen and Water in a Waste Incinerator for Active Combustion Control Purposes" $27^{th}$ Symposium on Combustion pp. 1301-1308.

Ebert et al. (2000) "Simultaneous Diode-Laser-Based in situ Detection of Multiple Species and Temperature in a Gas-Fired Power Plant" Proceedings of the Combustion Institute 28:423.

Ebert et al. (2000) *The Use of Lasers as the Basis for Combustion Equipment Control* at TOTem, Intelligent Combustion Control pp. 1-15.

Furlong et al. (1998) "Real-Time Adaptive Combustion Control Using Diode-Laser Absorption Sensors" $27^{th}$ Symposium on Combustion pp. 103-111.

Furlong, et al. (1998) Diode Laser Sensors for Real-Time Control of Pulsed Combustion Systems: AIAA/SAE/ASME/ASEE Joint Propulsion Conference and Exhibit, pp. 1-8, XP001148178, Jul. 13, 1998.

Liu et al. (2003) $39^{th}$ AIAA/ASME/SAE/ASEE Joint Propulsion Conference and Exhibit, Paper No. AIAA-2003-4581 pp. 1-6.

Miller et al. (1996) "Diode laser-based air mass flux sensor for subsonic aeropropulsion inlets" Applied Optics 35:4905.

Ouyang, et al. (1992) "Tomographic Absorption Spectroscopy of Combustion Gases Using Tunable Infrared Diode Lasers" Paper No. 1637-20, SPIE Conference on Environmental and Process Monitoring Technologies, pp. 163-172.

Phillippe et al. (1993) "Laser diode wavelength-modulation spectroscopy for simultaneous measurement of temperature, pressure, and velocity in shock-heated oxygen flows" Applied Optics 32:6090.

Sanders et al. (2000) "Diode-Laser Sensor for Monitoring Multiple Combustion Parameters in Pulse Detonation Engines" Proceedings of the Combustion Institute 28:587.

Sanders et al. (2001) "Diode-laser absorption sensor for line-of-sight gas temperature distributions" Applied Optics 40:4404.

Teichert et al. (2003) "Simultaneous in situ measurement of CO, $H_2O$, and gas temperatures in a full-sized coal-fired power plant by near-infrared diode lasers" Applied Optics 42:2043.

Upschulte et al. (1999) "Measurements of CO, $CO_2$, OH, and $H_2O$ in room-temperature and combustion gases by use of a broadly current-tuned multisection InGaAsP diode laser" Allied Optics 38:1506.

Varghese, et al. (1997) "Temperature and CO2 Concentration Profiles in Flames Measured by Laser Absorption Tomography" Paper 97/0317, AIAA $35^{th}$ Aerospace Sciences Meeting, Reno, NV, Jan. 1997.

Villarreal, et al. (2005) "Frequency Resolved Absorption Tomography with Tunable Diode Lasers" Applied Optics 44, pp. 6786-6795.

Webber et al. (2000) "In Situ Combustion Measurements of CO, $CO_2$, $H_2O$ and Temperature Using Diode Laser Absorption Sensors" Proceedings of the Combustion Institute 28:407.

Wolfrum (1998) "Lasers in Combustion: From Basic Theory to Practical Devices" $27^{th}$ Symposium on Combustion pp. 1-41.

Patent Abstracts of Japan, retrieved Aug. 8, 2008 from the Internet at URL http://www19.ipdl.inpit.go.jp/PA1/result/detail/main/wAAADta08RDA412074830.

Translation of portions of "Notice of Reasons for Rejection," mailed Aug. 5, 2008 by the Japan Patent Office prepared for Japan Patent Application No. 2006-509589, 4 pages.

* cited by examiner

METHOD FOR THE MONITORING AND CONTROL OF A PROCESS

RELATED APPLICATIONS

This application is a continuation of U.S. patent application Ser. No. 10/543,288 filed on Jul. 25, 2005 entitled "Method And Apparatus For The Monitoring And Control Of Combustion", which is a 371 of international patent application no. PCT/US04/10048 filed on Mar. 31, 2004 entitled "Method And Apparatus For The Monitoring And Control Of Combustion", which is a nonprovisional of U.S. Provisional Patent Application No. 60/459,108 filed on Mar. 31, 2003 entitled "Echelle Grating Optical Multiplexer with Widely Spaced Wavelengths".

TECHNICAL FIELD

The present invention is directed toward a method for the monitoring and control of a process, and more particularly toward the use of tunable diode laser absorption spectroscopy to monitor and control combustion processes.

BACKGROUND ART

A large percentage of the electrical power generated in the United States of America is created in coal combustion power plants. The bulk of worldwide electricity production similarly relies on coal as a primary energy source. It is likely that coal will remain a primary energy source in the foreseeable future given the long term environmental concerns with the storage of waste from nuclear energy generation operations, and the inefficiencies associated with solar powered electrical generation. In addition vast worldwide coal reserves exist sufficient for at least 200 years of energy production at current rates.

However, there is and will continue to be a high demand to reduce the emissions of pollutants associated with coal fired electrical energy generation, and to increase the overall efficiency of the coal fired generation process. Traditionally, in power plants and other industrial combustion settings the efficiency of the combustion process and the level of pollution emission have been determined indirectly through measurements taken on extracted gas samples with techniques such as non-dispersive infrared (NDIR) photometry. Extractive sampling systems are not particularly well suited to closed loop control of a combustion process since a significant delay can be introduced between the time of gas extraction and the ultimate analysis. In addition, extractive processes generally result in a single point measurement which may or may not be representative of the actual concentration of the measured species within what can be a highly variable and dynamic combustion process chamber.

Laser based optical species sensors have recently been implemented to address the concerns associated with extraction measurement techniques. Laser based measurement techniques can be implemented in situ and offer the further advantage of high speed feedback suitable for dynamic process control. A particularly promising technique for measuring combustion gas composition, temperature and other combustion parameters is tunable diode laser absorption spectroscopy (TDLAS). TDLAS is typically implemented with diode lasers operating in the near-infrared and mid-infrared spectral regions. Suitable lasers have been extensively developed for use in the telecommunications industry and are, therefore, readily available for TDLAS applications. Various techniques of TDLAS which are more or less suitable for the sensing and control of combustion processes have been developed. Commonly known techniques are wavelength modulation spectroscopy, frequency modulation spectroscopy and direct absorption spectroscopy. Each of these techniques is based upon a predetermined relationship between the quantity and nature of laser light received by a detector after the light has been transmitted through a combustion process chamber and absorbed in specific spectral bands which are characteristic of the gases present in the process or combustion chamber. The absorption spectrum received by the detector is used to determine the quantity of the gas species under analysis plus associated combustion parameters such as temperature.

For example, Von Drasek, et al., United States Patent Application Serial No. 2002/0031737A1, teaches a method and apparatus of using tunable diode lasers for the monitoring and/or control of high temperature processes. Von Drasek features the use of direct absorption spectroscopy to determine the relative concentration of numerous combustion species, temperature and other parameters. Calabro, U.S. Pat. No. 5,813,767, teaches a similar system for monitoring combustion and pollutants developed in a combustion chamber. Calabro utilizes an indirect spectroscopy technique wherein observed Doppler broadening of the shape of an absorption feature serves as the basis for temperature analysis.

Teichert, Fernholz, and Ebert have extended the use of TDLAS as a known laboratory analysis technique to a workable field solution suitable for the sensing of certain combustion parameters within the boiler fireball of a full sized coal fired power plant. In their article, "Simultaneous in situ Measurement of CO, $H_2O$, and Gas Temperature in a Full-Sized, Coal-Fired Power Plant by Near-Infrared Diode Lasers," (Applied Optics, 42(12):2043, 20 Apr. 2003) the authors present a successful implementation of direct absorption spectroscopy at a coal fired power plant and discuss certain technical challenges resulting from the extremely large scale and violent nature of the coal burning process. In particular, typical coal fired power plants have combustion chamber diameters of 10-20 meters. The plants are fired by pulverized coal, which results in a combustion process which both obscures the transmission of laser light because of the high dust load and which is extremely luminous. In addition, various strong disturbances are found under power plant combustion conditions. The overall transmission rate of light through the process chamber will fluctuate dramatically over time as a result of broadband absorption, scattering by particles or beam steering owing to refractive-index fluctuations. There is also intense thermal background radiation from the burning coal particles which can interfere with detector signals. The environment outside of the power plant boiler also makes the implementation of a TDLAS sensing or control system problematic. For example, any electronics, optics or other sensitive spectroscopy components must be positioned away from intense heat, or adequately shielded and cooled. Even though the implementation of a TDLAS system is extremely difficult under these conditions, TDLAS is particularly well suited to monitor and control a coal combustion process. The present invention is directed to overcoming one or more of the TDLAS implementation problems discussed above.

SUMMARY OF THE INVENTION

One embodiment is a method of sensing a process utilizing more than one diode laser having select lasing frequencies, a multiplexer optically coupled to the outputs of the diode lasers with the multiplexer being further optically coupled to a pitch side optical fiber. Multiplexed laser light is transmitted through the pitch side optical fiber to a pitch optic operatively associated with a process chamber which may be a combustion chamber or the boiler of a coal or gas fired power plant. The pitch optic is oriented to project multiplexed laser output through the process chamber. Also operatively oriented with the process chamber is a catch optic in optical communication with the pitch optic to receive the multiplexed laser output projected through the process chamber. As used herein, "coupled", "optically coupled" or "in optical communication with" is defined as a functional relationship between counterparts where light can pass from a first component to a second component either through or not through intermediate components or free space. The catch optic is optically coupled to an optical fiber which transmits the multiplexed laser output to a demultiplexer. The demultiplexer demultiplexes the laser light and optically couples the select lasing frequencies of light to a detector with the detector being sensitive to one of the select lasing frequencies. Optionally, the method may be implemented with each diode laser optically coupled to a distinct corresponding input optical fiber prior to the multiplexer and the detector optically coupled to an output fiber of the demultiplexer. The pitch side optical fiber may be a single mode fiber, and the catch side optical fiber may be a multimode fiber. Optionally, the method may also utilize a pitch side optical routing device optically coupled to the pitch side optical fiber and routing the multiplexed laser output to more than one pair of pitch and catch optics operatively associated with the process chamber. The optical routing device may be an optical switch, an optical splitter, or other commonly available off the shelf telecommunications optical routing apparatus. Optionally, the method may further include use of a data processing system receiving input from the detector and employing commonly known laser spectroscopy techniques to determine a combustion parameter from the detector data. The method may also include affecting the combustion parameter based upon the output of the data processing system. For example, the method may provide for closed loop control of a combustion input such as air flow, fuel flow or catalyst or chemical agent addition which control is responsive to the data processing system in accordance with the combustion parameter determined by the data processing system.

The method may utilize an echelle grating in the multiplexer or demultiplexer. Additional components of the multiplexer or demultiplexer may include an optical wave guide and a collimating focusing optic. The reflective echelle grating coupled to the collimating/focusing optic will typically have a groove spacing and blaze angle providing for the simultaneous demultiplexing of a plurality of ranges of widely spaced wavelengths of light. An appropriate echelle grating will typically be capable of multiplexing or demultiplexing wavelengths equal to or greater than 670 nm through wavelengths equal to or less than 5200 nm. To accomplish this, the echelle grating will operate at orders of defraction from the second order to at least the fourteenth order. Such an echelle grating will typically have a groove spacing of approximately 171.4 lines per mm and a blaze angle of approximately 52.75 degrees.

Optionally, the method may include having the multiplexer optically coupled to fewer than all of the diode lasers and further consist of an optical coupler coupled to the output of the multiplexer and the separate output of any unmultiplexed diode laser. In such an optional embodiment, the optical coupler will optically communicate with the pitch optic through a select length of transmitting optical fiber. The length of the transmitting optical fiber may be selected to minimize mode noise. For example, the transmitting optical fiber may be implemented at a length of equal to or less than 3 meters, and be fabricated of Corning SMF 28 optical fiber which will assure that wavelengths less than 1240 nm, in particular 760 nm, do not become multi-modal during transmission through the transmitting optical fiber.

The method may also include the mechanical manipulation of a section of the catch side optical fiber to minimize catch side mode noise. One example of an appropriate technique to mechanically manipulate a section of the catch side optical fiber consists of a motor having a shaft parallel to the longitudinal axis of the catch side optical fiber which is attached to the fiber and provides a twisting motion around the longitudinal axis. The twisting motion may consist of a sweep through plus 360 degrees and minus 360 degrees at a rate of at least 10 Hz to effectively average the transmitted signal and thereby reduce catch side mode noise.

Optionally, the method may further include use of a catch side alignment mechanism associated with the catch optic providing for the alignment of the catch optic with respect to the direction of the projection of the multiplexed laser output. The alignment mechanism may increase the quantity of laser light received by the catch optic from the pitch optic and thereby coupled to the catch side optical fiber. The alignment mechanism may consist of an apparatus which allows the catch optic to tilt along a first axis and a second axis orthogonal to the first axis with both the first and second axes being substantially orthogonal to the direction of the projection of the multiplexed laser output. A stepper motor may be used to tilt the catch optic and a data processing system may be further associated with the catch side alignment mechanism and receive data from the detector related to the strength of the multiplexed laser output coupled to the detector and cause the catch side alignment mechanism to align the catch optic. Alternatively, a separate alignment beam may be projected to the catch optic and used as a reference for alignment purposes. A similar alignment mechanism may be implemented on the pitch side of the sensing apparatus to provide for alignment of the pitch optic and adjustment of the direction of the projection of the multiplexed laser output.

DETAILED DESCRIPTION OF THE PREFERRED EMBODIMENT

Sensing Apparatus

Figure 1:
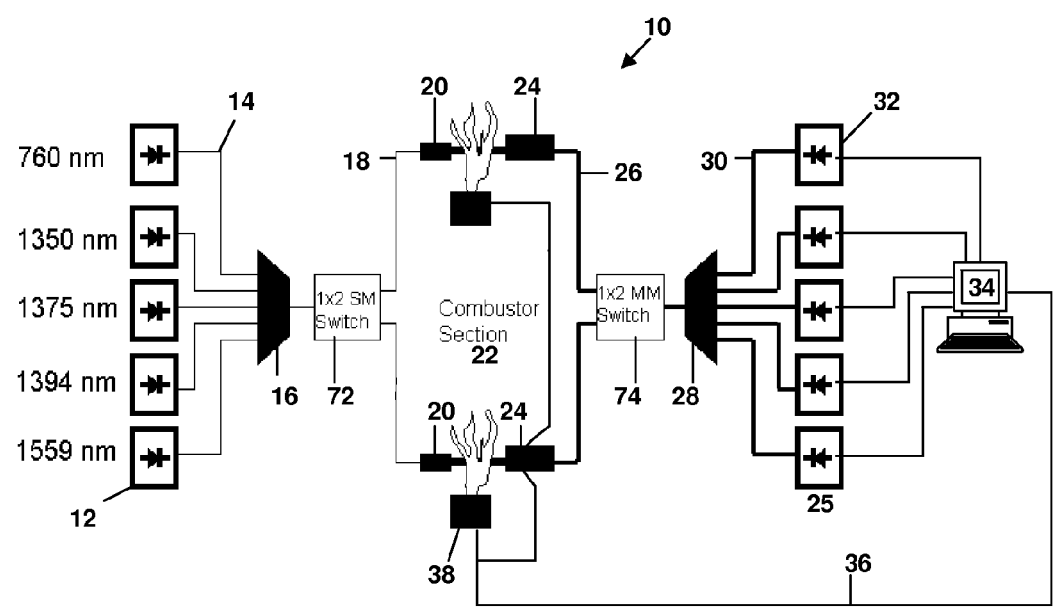
FIG. 1 is a schematic diagram of a sensing apparatus of the present invention.

As shown in FIG. 1 an embodiment of the present invention is a sensing apparatus 10 suitable for the sensing, monitoring and control of a combustion process. The sensing apparatus 10 performs tunable diode laser absorption spectroscopy (TDLAS) using laser light from a series of tunable diode lasers 12 lasing at select frequencies in the near-infrared or mid-infrared spectrum. The output of each tunable diode laser 12 is coupled to an individual optical fiber which may be a single mode optical fiber 14 and routed to a multiplexer 16. As used herein, "coupled", "optically coupled" or "in optical communication with" is defined as a functional relationship between counterparts where light can pass from a first component to a second component either through or not through intermediate components or free space. Within the multiplexer 16 the laser light of some or all of the frequencies generated is multiplexed to form a multiplexed probe beam having multiple select frequencies. The multiplexed probe beam is coupled to a pitch side optical fiber 18 and transmitted to a pitch optic 20 or collimator operatively associated with a process chamber which, in FIG. 1, is shown as a combustion chamber 22.

The pitch optic 20 is oriented to project the multiplexed probe beam through the combustion chamber 22. Across the combustion chamber 22 in optical communication with the pitch optic 20 is a catch optic 24. The catch optic 24 is preferably substantially opposite the pitch optic 20 and is operatively associated with the combustion chamber 22. The catch optic 24 is positioned and oriented to receive the multiplexed probe beam projected through the combustion chamber 22. The catch optic 24 is optically coupled to a catch side optical fiber 26 which transmits the portion of the multiplexed probe beam which is received by the catch optic 24 to a demultiplexer 28. Within the demultiplexer 28 the portion of the multiplexed probe beam received by the catch optic 24 is demultiplexed and each wavelength of demultiplexed laser light is coupled to an output optical fiber 30. Each output optical fiber 30 in turn is optically coupled to a detector 32, which typically is a photodetector sensitive to one of the select frequencies of laser light generated and multiplexed to form the probe beam. The detectors 32 generate an electrical signal based upon the nature and quantity of light transmitted to the detector 32 at the detector frequency. The electrical signal from each detector 32 is typically digitized and analyzed in data processing system 34. As discussed in detail below, the digitized and analyzed data can be used to sense physical parameters within the process chamber including but not limited to the concentrations of various gas species and the combustion temperature within the combustion chamber 22. The data processing system 34 can further be used to send signals through a feedback loop 36 to combustion control apparatus 38 and thereby actively control select process parameters. In the case of a combustion process, the process parameters controlled can include fuel (e.g., pulverized coal) feed rates; oxygen feed rates and catalyst or chemical agent addition rates. The use of fiber optic coupling of the electronic and optical components on both the pitch and catch sides of the sensing apparatus 10 allows delicate and temperature sensitive apparatus such as the tunable diode lasers 12, detectors 32 and data processing system 34 to be located in a control room having a stable operating environment. Thus, only the relatively robust pitch and catch optics 20, 24 need be situated near the hostile environment of the combustion chamber 22.

Figure 2:
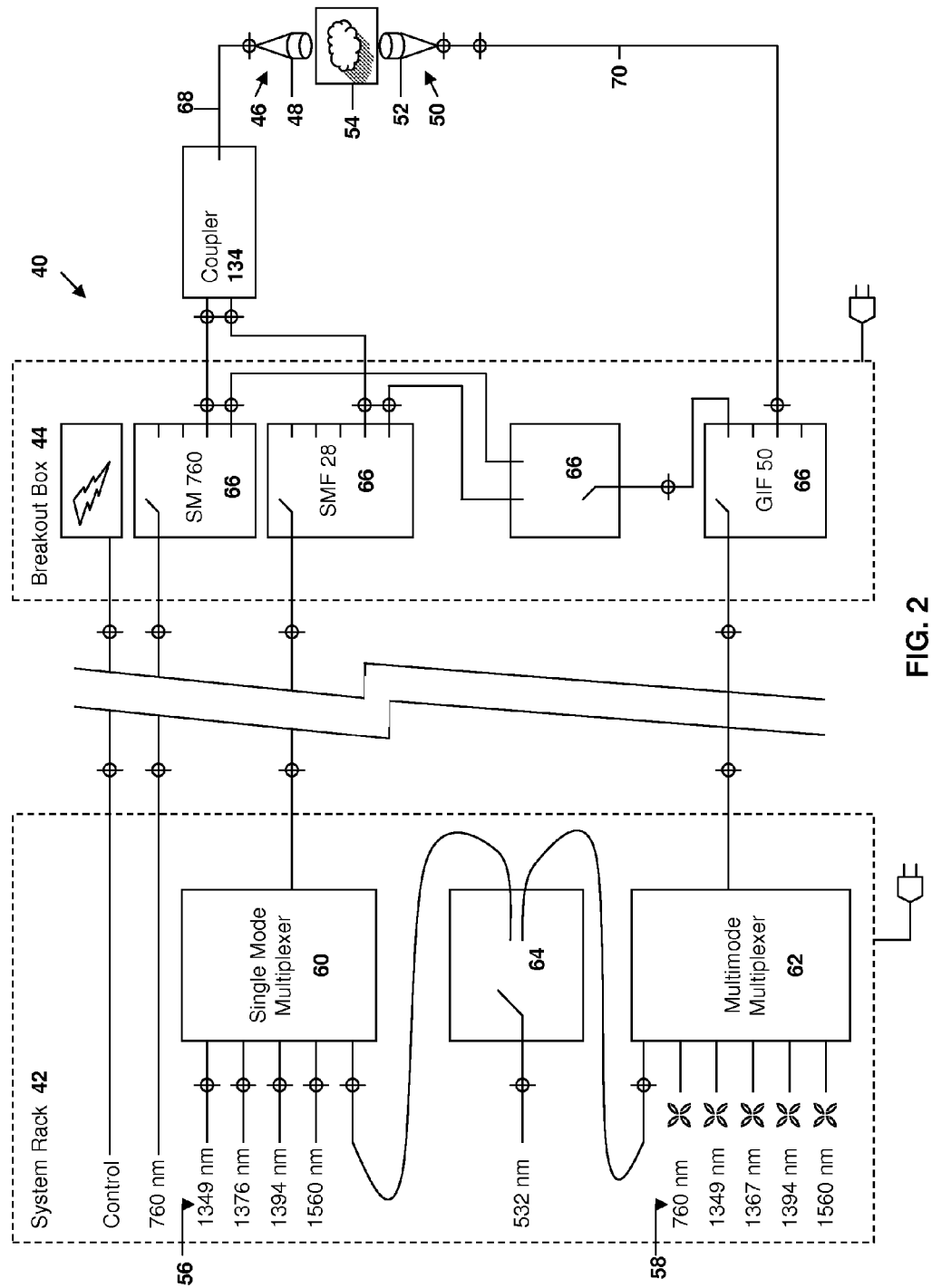
FIG. 2 is a schematic diagram of a sensing apparatus of the present invention featuring remotely located components optically coupled to components near the combustion chamber.

FIG. 2 schematically depicts the overall component placement of a fiber coupled, multiplexed sensing system 40. The sensing system 40 generally consists of a system rack 42, a breakout box 44, a transmitter head 46 having pitch optics 48, a receiver head having catch optics 52 and connecting optical fibers. The system rack 42 is preferably located in a remote control room situated a distance, for example one kilometer, from the combustion chamber 54. The control room typically will have a moderate environment. The system rack 42 contains the lasers 56, detectors 58, wavelength multiplexers 60 and wavelength demultiplexers 62. The system rack 42 also houses the system electronics and control software (not shown on FIG. 2). The system rack 42 may optionally house an alignment light source 64.

The optical fibers connecting the system rack 42 with the breakout box 44 are typically standard single-mode telecom optical fiber. This type of fiber is inexpensive, readily available, low-loss and allows the laser light to be directed to various off-the-shelf telecom components to manipulate the light, such as optical switches, splitters, and wavelength division multiplexers. Without optical fiber coupling, the laser light would have to be directed through free space all the way to the combustion chamber 54, which would be very difficult to implement or, alternatively, sensitive electronic and optical components would have to be situated in close proximity to the combustion chamber 54.

Also shown on FIG. 2 is a breakout box 44. The breakout box 44 is a ruggedized enclosure located close to the boiler. The breakout box 44 contains optical switches, splitters and couplers (collectively 66) which may be used as discussed below to direct the optical signals to multiple transmitter-receiver head pairs.

A third group of system components as shown on FIG. 2 are the transmitter and receiver heads 46, 50. The optics and electronics in the transmitter and receiver heads 46, 50 must convert the light in the fiber 68 into a collimated beam, direct the beam accurately through the combustion chamber 54, capture the beam on the far side of the combustion chamber 54 and couple the beam into the fiber 70. The choice of optics to accomplish this is determined by the transmission distance, the turbulence of the combustion zone, its effect on the transmitted beam's quality, and the core size of the fiber 70. Preferably, the fiber core diameter is 50 microns, which is a compromise: a larger core will capture more of the laser light but also much more of the background light. Fiber coupling on the catch (receiver) side has several advantages. In particular, only light in the same location as the laser light and traveling in the same direction is focused into the fiber 70. This drastically reduces the amount of background light that is sensed. In an alternative embodiment, light may be captured into one of several receiver fibers and an optical switch or other optical routing device can select light from one fiber for routing to the detectors 58.

The use of fiber coupling at the catch side requires that the alignment tolerances of both the transmitter and receiver optics be precisely maintained (less than 0.5 milliradian for both the transmitter and receiver pointing). The alignment system discussed below makes it feasible to meet these tolerances in a harsh power plant environment. Preferably, both the pitch and catch optics 48, 52 are custom-designed and aberration-corrected for wavelengths from 660 nm to 1650 nm so that multiple laser signals can be efficiently transmitted and received at the same time.

Sensing Apparatus with Multiple Sets of Sensing Optics

Referring again to FIG. 1, an embodiment is depicted schematically which features more than one set of pitch optics 20 and catch optics 24 associated with a single combustion chamber 22. The multiplexed probe beam can be routed by a routing device which, as is shown in FIG. 1, may be an optical switch 72 to each set of pitch optics 20. Suitable routing devices include optical switches which may be implemented to route the probe beam with minimal attenuation to each set of pitch/catch optics in a predetermined sequence or an optical splitter which simultaneously routes a fractional portion of the multiplexed probe beam to each set of optics.

Figure 3:
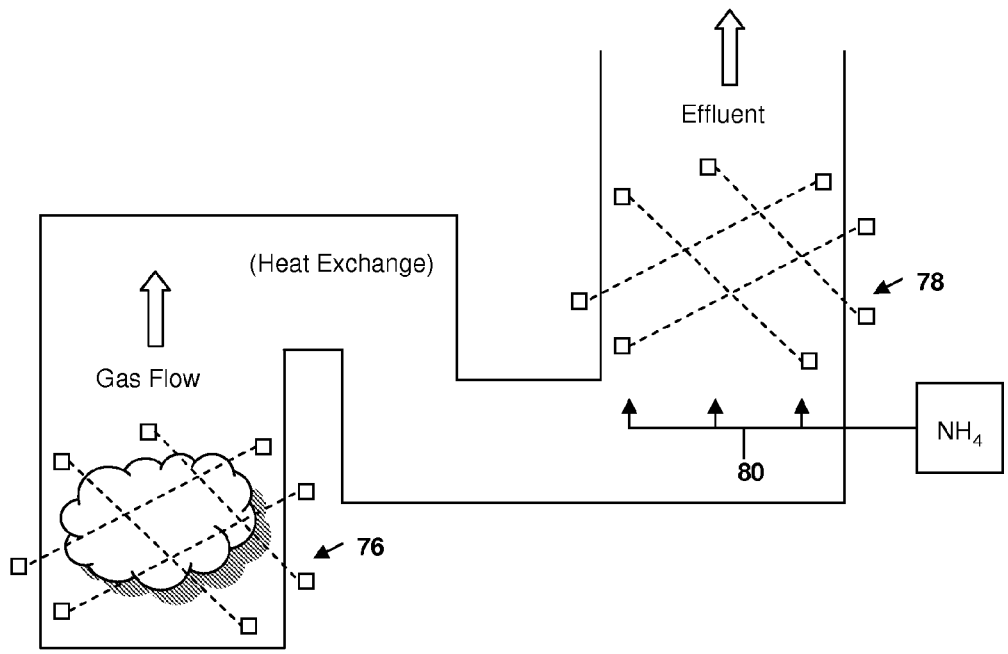
FIG. 3 is an illustration of an aspect of the present invention featuring multiple sensing grids.

A similar optical routing device which, in FIG. 1, is shown as a multimode optical switch 74 can be employed on the catch side of the system to route the portion of the multiplexed probe beam received by each catch optic 24 to the catch side demultiplexer 28. Although the embodiment depicted in FIG. 1 shows only two sets of pitch and catch optics, the system can employ any number of pitch and catch optical sets. The use of fiber coupling and a (de)multiplexed probe beam on both the pitch and catch sides of the system allows multiple sets of pitch and catch optics to be implemented with one set of lasers 12 and detectors 32. Without the incorporation of optical multiplexing techniques, separate sets of lasers, detectors and fiber cables, all requiring calibration, would be needed for each transmitter/receiver pair. As discussed in detail below, multiple transmitter/receiver pairs allow the implementation of one or more two dimensional sensing grids over the entire combustion chamber 22 or elsewhere, such as for sensing a downstream gas process. A schematic illustration of two highly simplified sensing grids, a fireball sensing grid 76 and a downstream sensing grid 78 are shown in FIG. 3. In addition, the fiber-coupled nature of the present invention allows readily available telecommunications components to be used to positive effect. For instance, a fiber-optics switch can be used to route the multiplexed probe beam to different locations for measurement. $1 \times N$ optical switches with N up to 8 are readily available as off-the-shelf components from a variety of suppliers. Switches with N up to 16 can be custom ordered.

A switch and multiple pairs of pitch and catch optics can be used for serial probing of a gas species at different locations throughout the combustion chamber. For situations in which averaged results are sufficient, serial probing of different beam paths is acceptable. However, certain applications require instantaneous probing of an entire sensing grid. For example, certain combustion process flows exhibits high-frequency fluctuations, or the flow may only exist for a short period of time, e.g. shock tubes or tunnels. In such a case a $1 \times N$ splitter may be used to divide the probe beam into N branches each of which occupies a different position on the grid. Since the entire grid is illuminated simultaneously, a two dimensional analysis can be generated very quickly. However, simultaneous two dimensional analysis may require that each component on the catch side be reproduced for each beam path including demultiplexers, detectors, electronics such as A/D cards and, to some extent, computers.

Thus, embodiments featuring switches or splitters facilitate somewhat coarse tomographic reconstruction of two-dimensional cross sections of the probed region. Using diode lasers to do tomography of gas concentrations is a known technique, however significant additional benefit is achieved under the present invention as a result of the use of a probe beam which is wavelength multiplexed. The wavelength multiplexed beam allows for the simultaneous spectroscopic analysis of more than one absorption line. Thus TDLAS techniques which rely on more than one line, such as temperature determination, as discussed in detail below, can be performed across the entire sensing grid. Both temperature and gas species concentrations can be mapped in this way.

Specific Application of Tomography in SCR and SNCR

A specific application of coarse tomography as described above is schematically illustrated in FIG. 3 and concerns the optimization of ammonia injection in SCRs (selective catalytic reduction) and SNCRs (selective non-catalytic reduction) for the reduction of $NO_x$ from coal or gas fired power generation boiler effluent. In this application, a matrix of ammonia or urea injectors 80 are placed in the flow of boiler effluent. In order to minimize the $NO_x$ concentration, an excess of ammonia (or urea) may be added to the effluent. $NO_x$ is a heavily regulated and highly undesirable family of air pollutants. The added ammonia chemically reduces the $NO_x$ and forms harmless nitrogen gas and water as products. However, the amount of excess ammonia (or urea) added must be minimized because these chemicals themselves are toxic air pollutants and quite expensive. Typically an excess concentration of <3-5 ppm ammonia is desired. However, the distribution of $NO_x$ in the power plant combustion effluent is not uniform, nor is it temporally stable. In addition, one or more of the ammonia injectors may foul at any given time causing a local decrease in the ammonia concentration leading to a local bleed through in the $NO_x$ concentration. With the ability to monitor the spatial concentration of ammonia or $NO_x$ with a downstream TDLAS grid 78 sensing as described above, the present invention allows non-uniform ammonia distributions to be detected and mitigated. Thus, optimization of the ammonia injection grid 76 with two-dimensional species concentrations and individual control over injectors allows the optimization of the SCR/SNCR process. The detectors and ammonia injectors may be linked to a data processing system providing automated feedback control of the ammonia injectors.

An optimized ammonia slip detection system, such as the one described herein, should preferably include the ability to monitor $NO_x$ concentration. $NO_x$ includes both NO and $NO_2$. Unfortunately, robust NIR diode lasers can only access the second NO overtone transition occurring in the 1.7-1.8-micron region. This transition is too weak to detect NO given the relatively low concentrations present in most effluent flows. Therefore it is not practical to directly monitor NO concentration. However, $NO_2$ is formed by the same processes that form NO. These processes, known in the power generation industries as the thermal $NO_x$ process produce both NO and $NO_2$ with NO accounting for approximately 95% of the total $NO_x$ concentration and $NO_2$ accounting for the remaining 5% under typical conditions. The exact ratio typically depends upon temperature and the oxidizing potential of the environment. As discussed above, this technique allows for determination of the temperature of the sampled gas as well However, it is expected that the NO and $NO_2$ concentrations will track each other. Thus $NO_2$ can be used as a surrogate analysis species for NO. The present invention provides the ability to monitor $NO_2$ at a wavelength of 670 nm. This wavelength is produced using a 1340-nm distributed-feedback (DFB) laser frequency-doubled in a phase-matched periodically poled lithium Niobate waveguide. Even though the $NO_2$ concentration is only 5% the NO concentration, the $NO_2$ absorption strength is orders of magnitude stronger. Thus, $NO_2$ can be detected readily at the concentrations present in boilers to facilitate optimization of $NO_x$ reduction processes.

Tunable Diode Laser Absorption Spectroscopy

The present invention performs TDLAS using techniques known to those skilled in the art of laser spectroscopy. Generally, TDLAS is performed by the transmission of laser light through a target environment, followed by the detection of the absorption of the laser light at specific wavelengths, due to target gases such as carbon monoxide or oxygen. Spectral analysis of the detected light allows identification of the type and quantity of gas along the laser path. The details of direct absorption spectroscopy are discussed in Teichert, Fernholz, and Ebert, "Simultaneous in situ Measurement of CO, $H_2O$, and Gas Temperature in a Full-Sized, Coal-Fired Power Plant by Near-Infrared Diode Lasers," (Applied Optics, 42(12):2043, 20 Apr. 2003), which reference is incorporated herein in its entirety. The non-contact nature of laser absorption spectroscopy makes it well-suited for harsh environments such as the combustion zone of a coal-fired power plant, or flammable or toxic environments where other probes cannot be used. The use of laser light provides the high brightness necessary to get detectible transmission in the presence of severe attenuation (typically greater than 99.9% loss of light) that may be seen in some of these environments. To better withstand the harsh conditions of the target applications, the laser light may be brought in to the target environment through armored optical fiber.

Effective sensing of temperature or multiple combustion process component gasses requires the performance of TDLAS with multiple widely spaced frequencies of laser light. The frequencies selected must match the absorption lines of the transitions being monitored. For example, as discussed above it is useful to monitor $NO_2$ at a wavelength of 670 nm to approximate emission NO concentrations. It is also quite useful to monitor oxygen, water (temperature), and carbon monoxide in a coal-fired utility boiler. Suitable absorption lines, and thus suitable lasing frequencies can be selected based upon an assumption that the laser probe path length through a combustion chamber is equal to 10 meters and that the mole fraction of each species is CO (1%), $O_2$ (4%), $CO_2$ (10%), and $H_2O$ (10%). For frequency selection purposes, the process temperature can be assumed to be 1800 K which is slightly higher than what is typically observed in a coal fired plant, but the cushion serves as a safety factor in the calculations.

For example, three water absorption lines can be selected for TDLAS that meet the following criteria:

1. Lower state energy of .about.1000, 2000, and 3000 $cm^{-1}$ respectively

2. Provides a convenient absorbance of around 0.1-0.4 that, in turn, leads to approximately 20% beam absorption on resonance.

3. The optimum situation is to utilize transitions in the 1250 to 1650 nm region where inexpensive, high power, DFB diode telecommunications lasers are available.

4. The transitions must be well separated to allow for easy multiplexing.

5. The selected wavelength must be efficiently diffracted by the existing (de)multiplexer gratings.

Suitable water lines occur at the following wavelengths: TABLE-US-00001 TABLE 1 UNP Lower Grating Wave- Wave-State Absorption Effi-length number Energy Grating at 1800K ciency (nm) ($cm^{-1}$) ($cm^{-1}$) Order and 10 M (model) 1349.0849 7412.432 1806.67 6.87 19.7% 81% 1376.4507 7265.062 3381.662 6.73 28.1% 77% 1394.5305 7170.872 1045.058 6.65 6.8% 72%

No interference from any other combustion gases is anticipated. The most likely species to interfere, $CO_2$ was modeled and there are no strong, interfering lines in the 1.3-1.4 micron region.

Similarly, a suitable carbon monoxide line can be selected based on the work of Ebert referenced and incorporated above. A suitable carbon monoxide line is found at 1559.562 nm using the R(24) line in a coal-fired utility boiler. Selection of this line avoids interference from water and carbon dioxide. Known gratings are quite efficient in this wavelength region since it is in the optical communications C band. The absorbance at this wavelength is expected to be 0.7%.

In addition, oxygen can be measured at 760.0932 nm. The preferred (de)multiplexing grating efficiency calculates to be only 40% in this region, however suitable laser power should be available for reasonable measurement efficiency.

As discussed herein, the use of fiber coupling on both the pitch and catch sides of a TDLAS sensing apparatus requires critical alignment of the pitch and catch optics. Active alignment is preferably accomplished with a select alignment wavelength. One possible alignment wavelength is 660 nm because high power (45 mW) diodes are available at this frequency and 660 nm would be near the peak of $14^{th}$ order grating operation. Other alignment wavelengths may be determined to be equally or more suitable.

In summary, a reasonable set of wavelengths selected for multiplexing to a probe beam for TDLAS as embodied in the present invention are as shown in Table 2. It should be noted that this wavelength set is for one embodiment of a TDLAS sensing apparatus suitable for the sensing and control of a coal fired power plant. Other wavelength sets can be equally suitable. TABLE-US-00002 TABLE 2 Purpose Wavelength (nm) Alignment 660 $O_2$ b-a band 760.0932 $H_2O$ (moderate temp. line) 1349.0849 $H_2O$ (high temp. line) 1376.4507 $H_2O$ (low temp. line) 1394.5305 CO R(24) of (2, 0) overtone 1559.562

Specific Benefits of TDLAS Using Multiplexed Beam

A particular advantage of TDLAS with a wavelength-multiplexed probe beam is increased accuracy of temperature measurements. In order to make accurate concentration measurements with TDLAS, the temperature of the monitored gas must be known. The strength of a molecular absorption is a function of temperature. Thus, to convert the amplitude of an absorption feature to concentration, the temperature must be known. Certain previous attempts to measure the concentration of combustion species such as CO suffer from insufficiently accurate temperature measurements leading to errors in quantification. This is particularly true for diode laser based ammonia slip monitors that have traditionally not incorporated temperature measurement at all. In the sensing system of the present invention, temperature may be determined by measuring the ratio of the intensity of two or more molecular water lines. The ratio of the integrated intensity of two lines is a function of temperature only (assuming constant total system pressure). Thus, in principle, two lines provide an accurate temperature. However, in the case of a non-uniform temperature distribution (as is typically found within an industrial combustion process), two lines do not suffice to determine the temperature distribution. In such a non-uniform temperature distribution, two lines can only determine a "path-averaged" temperature. In contrast, measuring the integrated amplitude of more than two lines (of the same species) allows temperature non-uniformity to be probed. An example of this technique has been demonstrated using oxygen as the probe molecule by Sanders, Wang, Jeffries and Hanson in "Applied Optics" (vol. 40, num. 24, 20 Aug. 2001), which reference is incorporated herein in its entirety. The preferred technique relies on the fact that the distribution of peak intensities measured along a line of sight is not the same for a path at an average temperature of 500 K, for example, as it is where one half of the path is at 300 K and the other half is at 700 K.

In addition to the benefit of more accurate temperature measurement, the use of a multiplexed probe beam can allow for the simultaneous monitoring of more than one combustion gas species, allowing for more refined control over the combustion process.

Echelle Grating Based Apparatus

The present invention benefits from the use of relatively inexpensive and commonly available optical components designed for use in the telecommunications industry. The telecommunications apparatus serve well to fiber couple the pitch and catch sides of the system. Telecommunications applications typically use optical multiplexers which accept multiple light beams at wavelengths which are relatively close spaced and separated by a constant value (such as 0.8 nm). The light beams are then generally coupled onto a single-mode optical fiber. Demultiplexers perform the inverse process. Telecommunications equipment is typically designed to perform at wavelengths between 1520 and 1620 nm, with the Optical C-band, 1528-1563 nm, being the most utilized.

In the case of (de)multiplexers, the same physical device may be used for either multiplexing or demultiplexing, depending upon the direction of the light which passes through it. Consequently, the term "multiplexer" or "mux" as used herein will be understood to include both multiplexing and demultiplexing functions.

Optical multiplexers may use any of several technologies to accomplish the mux/demux function. However, echelle grating-based muxes are advantageous in that they may be incorporated into a very simple and compact design. Echelle gratings are relatively course diffraction gratings that operate in orders other than the first order with blaze angles typically greater than 45 degrees. The course line spacing on the grating combined with high order operation results in a large angular dispersion that allows the device to be compact.

Figure 4:
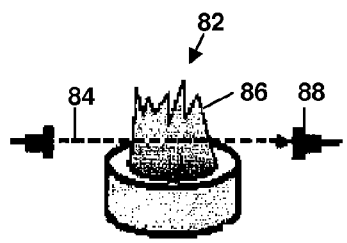
FIG. 4 is an illustration of a prior art single beam gas detection apparatus.

Some telecommunications applications may require that other wavelengths well outside of the C band be simultaneously serviced by optical multiplexers (for instance 1310 nm). Additionally, applications outside the telecommunications field such as the TDLAS sensing and control apparatus of the present invention may require the multiplexing of laser light at widely separated wavelengths, such as separations of approximately 100 s of nm. An example illustrative of the benefits of an echelle grating based multiplexed sensing apparatus is developed in FIGS. 4-7. FIG. 4 illustrates a gas sensing apparatus 82 in which light 84 is directed through a flame 86 from one side. A sensor 88 on the other side of the flame detects the transmitted light and determines how much light is absorbed by the gasses in the flame 86. In the device illustrated in FIG. 4, only a single beam of light is passed through the flame 86. The wavelength of the light may be chosen to correspond to the absorption wavelength of a particular gas. Alternatively, the light may be a white light which, after passing through the flame 86, is spit into various wavelengths, such as by a prism. The absorption at each wavelength of interest can then be measured.

Figure 5:
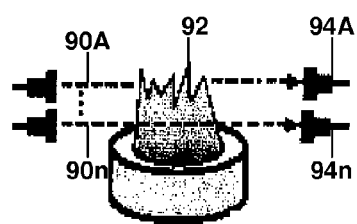
FIG. 5 is an illustration of a prior art multiple beam gas detection apparatus.

In a slightly more sophisticated prior art alternative, a device such as that illustrated in FIG. 5 may be used to pass a number n of separate beams of light 90A-90$n$ through the flame 92. Each beam of light 90A-90$n$ is at a different wavelength of interest and sensors 94A-94$n$ on the other side of the flame 92 measure the absorption at each wavelength, indicating relative amounts of selected gases of interest. There are several drawbacks to using multiple separate beams. First, access to the flame may be limited and attempting to project the multiple beams through the limited space may be awkward, if not impossible. Second, there is typically turbulence in the flame as well as pockets of non-uniformity. The multiple beams, even if very closely spaced, may not pass through the same sampling space and therefore not generate consistent or comparable results. Finally, the projection and sensing optics and detectors are more complex and costly in a multiple-beam apparatus compared to those in a single-beam apparatus.

The echelle grating multiplexer based sensing device of the present invention has significant advantages over the prior art. An echelle grating provides unusual flexibility by being able to operate in orders other than the first order with blaze angles typically greater than 45 degrees. For instance, the Zolo Technologies, Inc. Zmux.™ is optimized to operate in a Littrow configuration in the 6.sup.th order at 1545 nm with a mechanically ruled grating having a line spacing of 171.4 lines/mm and a blaze angle of 52.75 degrees. The grating equation for a Littrow mount is: m.lamda.=2d sin .theta..sub.b (1) where m is the order, .lamda. is the wavelength, d is the spacing between rulings, and .theta..sub.b is the blaze angle.

Figure 6:
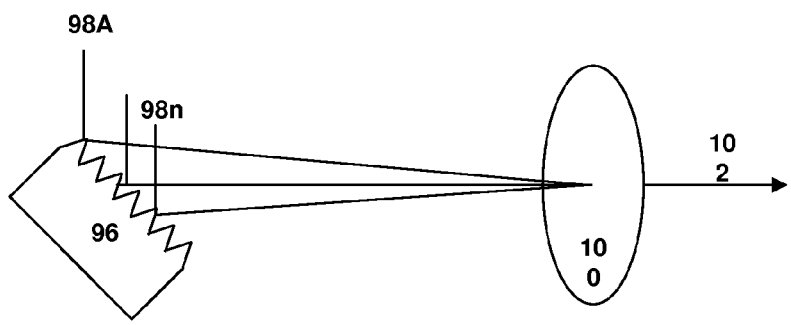
FIG. 6 is an illustration of the use of an echelle grating in the present invention.

For a given grating, m.lamda. is a constant. For the Zmux grating referenced above, m.lamda.=6(1.545)=9.27 microns. Such a grating provides optimum efficiency for 1.545 microns in 6.sup.th order. However, the grating also provides very high efficiency for other orders as well. For instance, the 7.sup.th order occurs at 9.27/7=1.32 microns. Thus, a grating such as the Zmux can simultaneously multiplex C band light as well as 1310 nm light with high efficiency. FIG. 6 illustrates an echelle grating 96 multiplexing light 98A-98$n$ to be collimated by a collimator 100 into a single beam 102.

Of particular relevance to the present invention are applications outside of the telecommunications field for multiplexing laser light at widely separated wavelengths, often over 100 s of nm. In applications such as the present TDLAS based gas-sensing apparatus, it is critical for all wavelength components of a probe beam to sample the same region of space and many wavelengths may be necessary to detect a single species or to detect multiple species. For these applications, echelle grating-based mux/demuxes provide a unique solution. For example, the echelle based de/multiplexer described above is capable of muxing a substantial wavelength region about the central wavelengths given in Table 3 below where each wavelength region corresponds to a different grating order. TABLE-US-00003 TABLE 3 Approximate Central Wavelength Order (microns) Range (microns) 2 4.63 4.40-4.80 3 3.09 2.90-3.30 4 2.32 2.15-2.40 5 1.85 1.70-1.95 6 1.55 1.50-1.57 7 1.32 1.24-1.39

Figure 7:
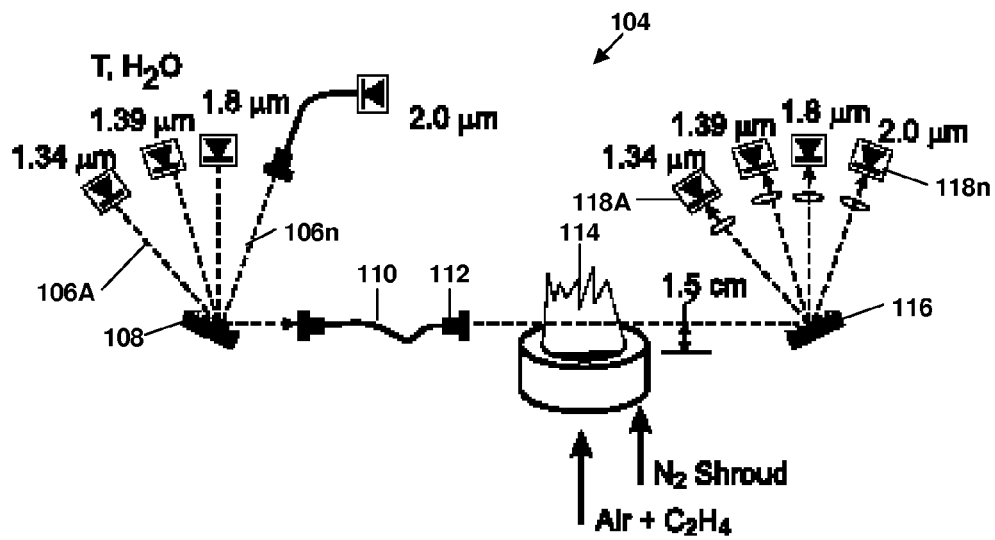
FIG. 7 is an illustration of an echelle grating based diode laser spectroscopy gas sensing apparatus of the present invention.

Higher orders up to and beyond the fourteenth order may also be multiplexed with correspondingly narrower wavelength ranges. It is noteworthy that single mode transmission for all of these wavelengths is not possible in readily available optical fiber. One aspect of a gas-sensing apparatus 104 of the present invention is schematically illustrated in FIG. 7. This aspect highlights the advantages of TDLAS with a multiplexed laser output has over the prior art embodiments discussed above. In the FIG. 7 embodiment, a number n of laser sources 106A-106$n$ operating at widely separated wavelengths are multiplexed by an echelle grating 108 onto a single optical fiber 110. The light from the single fiber 110 is collimated by a collimator or pitch optic 112 and passed through the sample 114 (such as a flame) to be analyzed. After passing through the sample 114, the light is demultiplexed by another echelle grating 116. The transmitted light at each wavelength is detected by a corresponding photodetector 118A-118n. The lasers 106A-106n are tuned over a narrow spectral region (such as 1-2 nm) and absorption by the sample 114 is monitored over each spectral region scanned. In this way, the gas under test can be fully identified and quantified. Other parameters such as gas temperature and pressure may be measured as well. In addition to combustion sensing, widely separated wavelength echelle grating mux/demux technology may enable medical devices to measure gases in exhaled breath and homeland defense devices to detect chemical warfare agents. Other applications are possible in the fields of display and microscopic vision technology by using the echelle based muxes and red/green/blue coupler devices.

Mode Noise

The optical train of the TDLAS system of the present invention, and similar implementations which require a signal multiplexed from widely spaced wavelengths presents many design challenges due to the opposing design requirements of the reduction of mode noise and high efficiency light collection. Mode noise is defined herein as a change in the signal level of detected light that results from non-uniform time and wavelength varying light distribution in the core of a fiber used to collect and transport the light to and from the process chamber being measured.

In a multimode fiber, different modes propagate at different velocities due to refractive index variations. The intensity distribution in the fiber is then a speckle pattern resulting from interference of all the propagating modes that have undergone different effective path lengths. If all light in the speckle pattern is collected and detected, then constructive and destructive interference cancel exactly and the total transmitted power does not depend on wavelength or fiber length. If clipping, vignetting or other loss is introduced, the exact cancellation fails and the detected power changes with wavelength and/or time. A general expression for the detected power after a length, $z$, of fiber is:

$$\rho = P_0 + \Sigma_{i,j} c_{ij} E_i E_j \cos[(2\pi \nu_0 \Delta n_{ij} z)/c + \Delta \phi_{ij}(T, \sigma)] \quad (2)$$

where $P_0$ = wavelength independent average power $E_i$ = amplitude of light in the ith transverse mode $c_{ij}$ = overlap integral between the ith and jth transverse mode $\Delta n_{ij}$ = refractive index difference between ith and jth modes $\Delta \phi_{ij}$ = phase shift between ith and jth modes due to temperature and stress For an orthonormal set of modes and no loss, $c_{ij} = 0$. However, with any beam clipping or vignetting or any other mode dependent loss will cause some $c_{ij} \neq 0$. This will lead to ripples in the average transmitted power.

For a typical graded-index fiber with a 50 micron core, the total index change, $\Delta n$, is about .1%, but most modes spend the bulk of transmission time close to the fiber core center, and therefore, $\Delta n_{ij} \leq 0.0005$, in general. The commonly available optical fiber GIF50 supports approximately 135 modes, which is sufficiently coarse to produce prominent mode noise during a wavelength scan given reasonably achievable beam clipping levels.

As a concrete modal noise example, one may consider the simplest possible system that exhibits mode noise: a rectangular waveguide supporting only the lowest mode in one dimension and only the two lowest modes in the orthogonal dimension: Lowest mode: $E_1 = E_1^0 [\exp i(kz - \omega t)] \cos \pi x/2a$ Next mode: $E_2 = E_2^0 [\exp i(kz - \omega t)] \sin \pi x/a$ The intensity at a point z along the fiber is: $I(x) = |E_1 + E_2|^2$ and the total power is $P = \int |E_1 + E_2|^2 dx$ (3) where the integral must include the effects of clipping and vignetting.

In the absence of clipping, $P \approx E_1^2 + E_2^2$ and there is no wavelength dependence. Adding clipping amounts to changing the limits of the integral. It can be shown that clipping results in an additional term $\approx E_1 E_2 \cos \Delta \phi$ where $\Delta \phi = \Delta kL = 2\pi \Delta nL/\lambda$.

If single-mode fiber could be used in the catch side optical train of the present invention, mode noise would not be an issue. However, multimode fiber must typically be used in the catch side optical train of the present invention for two reasons. First, after traversing the measurement volume (a combustion chamber with a measurement path in excess of 10 meters), the initially single-mode (Gaussian spatial distribution) beam is significantly degraded in quality. Thus, the coupling efficiency of this severely distorted beam into single-mode fiber would be very poor. This is an unacceptable situation since the beam is attenuated by 3-4 orders of magnitude when passing through the measurement volume primarily due to scattering and obscuration by soot and fly ash. The additional attenuation resulting from using single-mode fiber would preclude measurement. Second, refractive beam steering effects in the fireball cause the position and pointing of the beam to be unstable. Given these effects, it would be difficult to "hit" the core of a single-mode fiber with any regularity.

On the other hand, the core of a multimode fiber presents at least 25 times the target cross-sectional area of a single-mode fiber. Thus, the effects of beam steering can be significantly reduced. In addition, since the coupling efficiency into multimode fiber is independent of the spatial mode of the light, the poor beam quality obtained after passing through the fireball is not an issue.

However, mode dependent losses occurring in the multimode fiber train are a significant design challenge. The light distribution emanating from the core of a multimode fiber exhibits a random speckle pattern, i.e. a random pattern of light and dark areas caused by constructive and destructive interference between different modes of the fiber. If the speckle pattern was totally invariant as a function of time and wavelength, it would not present a problem. However, slow variations in the speckle pattern particularly as a function of wavelength can cause mode noise if the beam is clipped anywhere in the multimode catch side optical train as described above. This clipping is impossible to avoid; it can only be reduced. Therefore, additional measures to reduce mode noise must be implemented to improve the detection sensitivity of the system.

There are several ways in which to mitigate mode noise. From equation 2 above, mode noise may be reduced by:

1) reduce mode dependent losses, i.e. reduce clipping thereby keeping the $c_{ij}$ small 2) reduce $z$, thereby increasing the period of the model noise to be much greater than the absorption lines of interest 3) reduce $\Delta n_{ij}$ by using low dispersion fiber 4) scramble the modes; but not all mode scrambling techniques are equally effective, as is described below.

Preferably, the catch optics of the present invention are designed and implemented to incorporate all of the above in order to reduce modal noise. The optics are designed such that any beam clipping should occur at a low level given near perfect alignment of the system. Efforts should be made to keep the length of multimode fiber to a minimum; however, for some applications z must be long in order to have the control electronics in an environmentally controlled area. The value of $\Delta n_{ij}$ may be reduced by using premium low-dispersion multimode fiber. In addition, excellent results may be obtained by scrambling the modes by mechanical manipulation of a catch side multimode fiber.

The speckle pattern exhibited in a multimode fiber varies as a function of time and wavelength and also as a function of the mechanical position of the fiber. Flexing the fiber and manipulating it in specific ways can cause the speckle pattern to change. If these mechanical manipulations are performed continuously, over a period of time, the spatial distribution of light emanating from the fiber averages to a relatively uniform pattern. The crux of the scrambler of the present invention is to reduce mode noise by mechanically manipulating multimode fiber to produce, on average, a uniform light beam that does not produce mode noise when subjected to inevitable low-level beam clipping.

Some specific modes of fiber manipulation are more effective at reducing mode noise than others. In particular, twisting the fiber about its longitudinal (z) axis relative to some other point on the fiber causes the speckle pattern to change. In particular, the dominant change obtained is a rotation of the speckle pattern around the z-axis. Of interest is the fact that the pattern does not rotate as far around the axis as the fiber is mechanically rotated. A secondary effect is that the actual light distribution is somewhat altered by the rotation. The rotation of the speckle pattern is not due to stress-induced refractive index changes in the fiber, although this may explain small changes in the speckle intensity pattern. Rather, the rotation is due to the light's inability to completely follow the waveguide as it is manipulated in a torsional motion.

This observation can be used to virtually eliminate mode noise caused by the use of multimode fiber for the catch side optical train. A highly preferred embodiment of the present invention uses a hollow shaft motor through which the multimode fiber is placed and fastened. A remote section of fiber is held fast relative to the shaft position of the motor, and the motor is repetitively swept through +360 degrees and then −360 degrees of motion. The frequency of this motion preferably is greater than or equal to 10 Hertz to enable effective averaging of the transmitted signal, and significantly reduce the effect of catch side mode noise.

The pitch side optical train of the present invention also presents a significant design challenge due to the necessity of producing a single-mode beam for all wavelengths to be transmitted through the measurement region. If single-mode fiber could be used throughout the pitch side optical train, mode noise would not be an issue. However, fiber only operates as a single-mode waveguide over a limited wavelength window. Beyond the short wavelength cutoff for a particular fiber, light can be transported through the fiber in several higher order spatial modes. These higher order modes will interfere to produce a speckle pattern when the light exits the fiber. The speckle pattern is time and wavelength-varying. Even a small amount of beam clipping then gives rise to noise in the measurement.

On the contrary, if a fiber is selected that has a single-mode cutoff that matches the shortest wavelength that needs to be transmitted, the longer wavelengths will suffer a substantial loss when coupled into the fiber and the fiber will exhibit extensive bending losses for the longer wavelengths.

This problem can be acute in the fiber coupled, wavelength multiplexed TDLAS sensing and control device of the present invention due to the need to multiplex wavelengths as long as 1.67 microns with wavelengths as short as 760 nm or 670 nm. There is no known single commercially available fiber that will provide single mode operation, high coupling efficiency and low bending losses for such a broad range of wavelengths. Photonic crystal fiber may in the future provide a solution to this dilemma, but Photonic crystal fiber technology is currently in its infancy.

Figure 8:
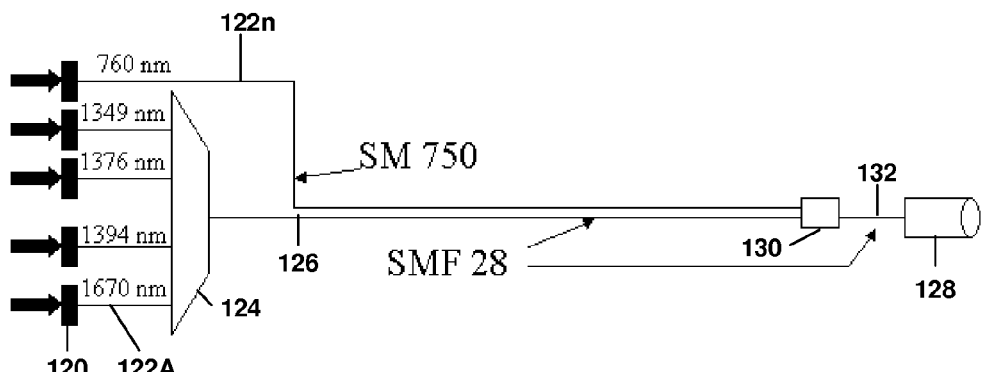
FIG. 8 is an illustration of a pitch side optical system suitable for minimizing mode noise.

As shown in FIG. 8, the current invention alleviates the problem of multiplexing and pitching light in a single mode beam from 670 m or 760 nm to 1.67 microns by utilizing a very short transmission section of multimode fiber 120 that does not allow the higher order spatial modes for a wavelength shorter than the single mode cutoff to develop. Referring to equation 2 above, if the length, L, of multi-mode fiber is short, then mode noise will be minimized. In this case, for example, if 760 nm light is coupled to a short section of single mode fiber with a cutoff wavelength of 1280 nm (e.g. Corning SMF 28), the 760 nm light remains single-mode for at least a few meters. Therefore a solution to pitch side mode noise is to couple the 760 nm light into a fiber which is single mode for wavelengths longer than 1280 nm but could be multimode for 760 nm, with only a short distance to go before it is collimated to be transmitted through the measurement zone.

A schematic diagram of such a system is shown in FIG. 8 and FIG. 2. Referring first to FIG. 8, multiple diode laser sources 120 lasing at widely spaced lasing frequencies are coupled to discrete single mode optical fibers 122A-122n. The diode lasers lasing at wavelengths between 1349 nm and 1670 nm are multiplexed with multiplexer 124. The output of multiplexer 124 is coupled to a pitch side fiber optic 126 having suitable dimensions for transmitting light with wavelengths ranging from 1349 nm-1670 nm, both without substantial transmission losses and without the introduction of mode noise. A suitable fiber optic for these wavelengths is Corning SMF28. However, the 760 nm input, if multiplexed and coupled to an SMF28 optical fiber would, after transmission over a relatively short distance, become multimodal. Accordingly, the output of the 760 nm laser is coupled to a fiber which is single mode for wavelengths less than 1280 nm such as SMF750. The laser light transmitted in the input fiber 122n and the multiplexed laser light transmitted in the pitch side optical fiber 126 can be coupled nearby the pitch optic 128. The coupler 130 and pitch optic 128 are preferably optically connected by a short length of transmission optical fiber 132 with the transmission optical fiber 132 being selected to transmit all of the coupled and multiplexed wavelengths without significant loss. A suitable transmission optical fiber for the system depicted in FIG. 8 would be Corning SMF28. Provided that the transmission optical fiber is relatively short, the 760 nm laser light coupled to the transmission optical fiber 132 will not exhibit multimodal behavior. For the system and fibers depicted in FIG. 8, it has been determined that the transmission optical fiber must be kept to a length of 3 meters or less to avoid the introduction of significant multimodal noise.

A similar system is shown in FIG. 2 where coupler 136 receives input from both a 760 nm diode laser and a multiplexed beam from diode lasers having substantially longer wavelengths.

Alignment System

Preferably, the sensing system of the present invention incorporates an auto alignment feature that allows the pitch and catch optics to maintain optimal alignment even though they are bolted on to a boiler or other hostile process chamber which is, itself, subject to movement from thermal effects, wind and vibration. In a highly preferred embodiment of the present system, both the pitch and catch optics are mounted on feedback-controlled tip/tilt stages. The requirement that both pitch and catch optics be mounted on tip/tilt stages results from the fact that the sensor is totally fiber-coupled. Thus, multiplexed light is launched across the measurement region by a collimating pitch optic attached directly to an input fiber, and the catch optic couples the transmitted light directly into an output fiber that typically is a multimode fiber. Accordingly, the catch optic must be oriented so that it is collinear with the beam emanating from the pitch optics. This is necessary so that the focused transmitted beam will arrive within the acceptance cone of the multimode catch fiber.

Figure 9:
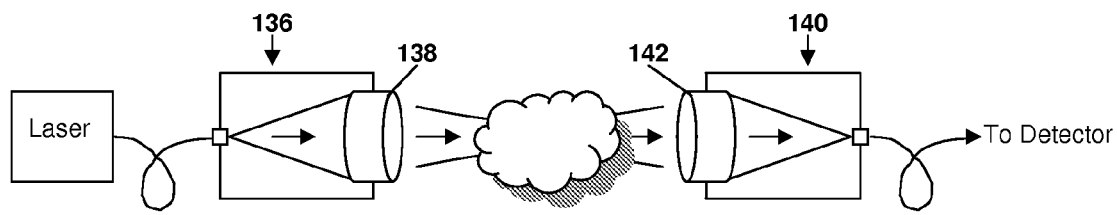
FIG. 9 is an illustration of a fiber coupled gas sensing apparatus.
Figure 10:
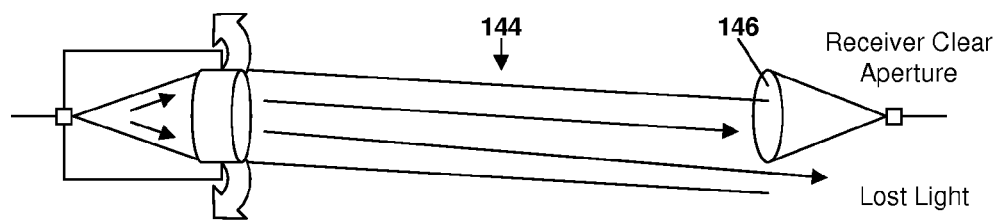
FIG. 10 is an illustration of light lost between pitch and catch optics.

In order to discriminate transmitted laser light from intense background light (for example, from the flames in a coal furnace), the field of view and focus of the detector can be limited to sense only light with the same direction and position as the input laser light. This may be done conveniently by focusing detected light into an optical fiber coupled to a suitable detector. The basic optical system design of an embodiment of the present invention is shown schematically in FIG. 9. The transmitter 136 of FIG. 7 consists of a pitch optic 138 or collimator such as a collimating lens of one or more than one layer and associated mounting and alignment structures and electronics. Similarly, the receiver 140 of FIG. 7 consists of a catch optic 142 or collimator of similar or varied construction from the pitch optic and associated mounting and alignment electronics. The efficiency and background discrimination of a transmitter-receiver pair are tied to alignment tolerance. For highest efficiency and discrimination, the alignment tolerances for both the transmitter and receiver are severe. The transmitter must be pointed accurately enough so that most of the transmitted light strikes the clear aperture of the catch optic 146, as indicated in FIG. 10. For a typical system, this amounts to a 1 cm tolerance over a typical transmission distance of 10 meters, or 1 milliradian. (With target distances between 5 and 30 meters and launched spot sizes between 1 and 3 cm, diffraction is a small contribution.)

Figure 11:
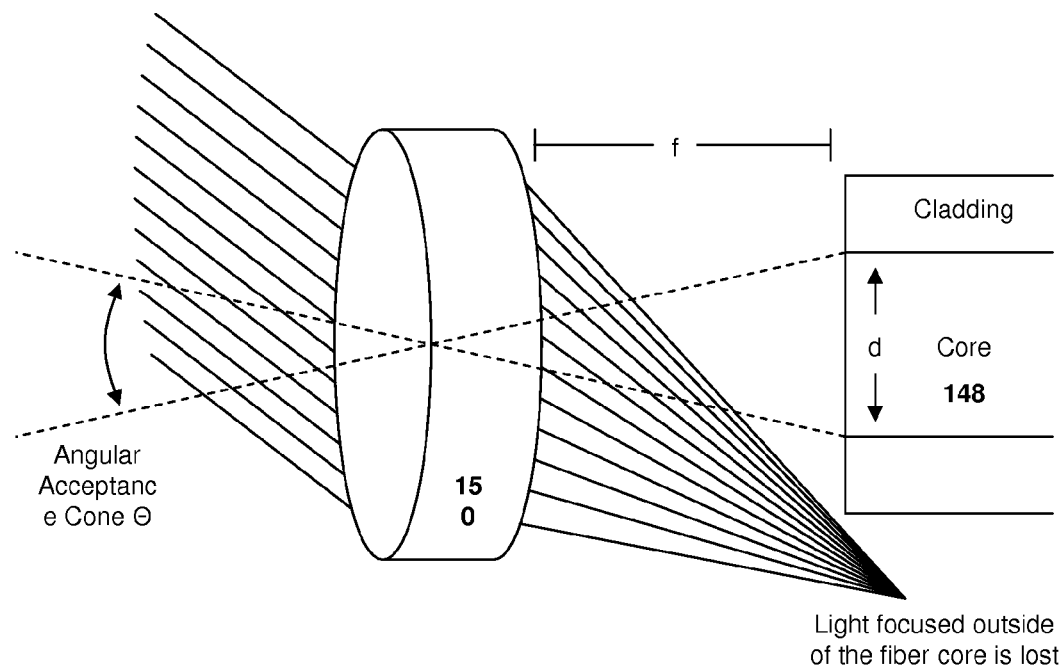
FIG. 11 is an illustration of the angular acceptance cone of a fiber optic system.

As is graphically illustrated in FIG. 11, the receiver's angular acceptance is determined by the fiber core 148 diameter divided by the catch optic 150 focal length. A shorter focal length will increase the angular acceptance, but the receiver clear aperture becomes correspondingly smaller. A compromise having adequate clear aperture and angular acceptance is to use a 50 mm focal length lens and a 50 micrometer core fiber. This results in a 2 cm clear aperture and a 1-milliradian cone of angular acceptance.

A preferred alignment system must therefore position two optics to point at each other with tolerances of 1 milliradian in both tip and tilt, for a total of four degrees of freedom. These four degrees of freedom might possibly be accomplished by rough alignment of one side followed by a four-dimensional alignment (tip, tilt, and lateral position in x and y) of the other side, but this assumes that large lateral motions are permissible. Since access ports for target environments may be as small as 1 inch, this is potentially a problematic solution. Alternatively, active pointing alignment at both ends can ensure proper alignment when limited space is available for lateral movement.

The critical alignment of the pitch and catch optics must be maintained in a harsh and variable environment. Vibration, wind loading, temperature change and other structural shifts may all lead to misalignments, as will mechanical creep in the transmitter and receiver optomechanics. Misalignment can also be expected after periodic maintenance, when the transmitter and receiver heads are removed for cleaning and then re-mounted. Ideally, the optical system of the present invention will be able to maintain its 1 milliradian optical alignment in the face of system misalignments that could approach 50 milliradians. The alignment system should also retain position during power outages and tolerate total loss of signal, and be turned off without losing alignment. Finally, the system itself must preferably be rugged enough to function continuously for an extended period of time in an exposed, industrial environment.

Figure 12:
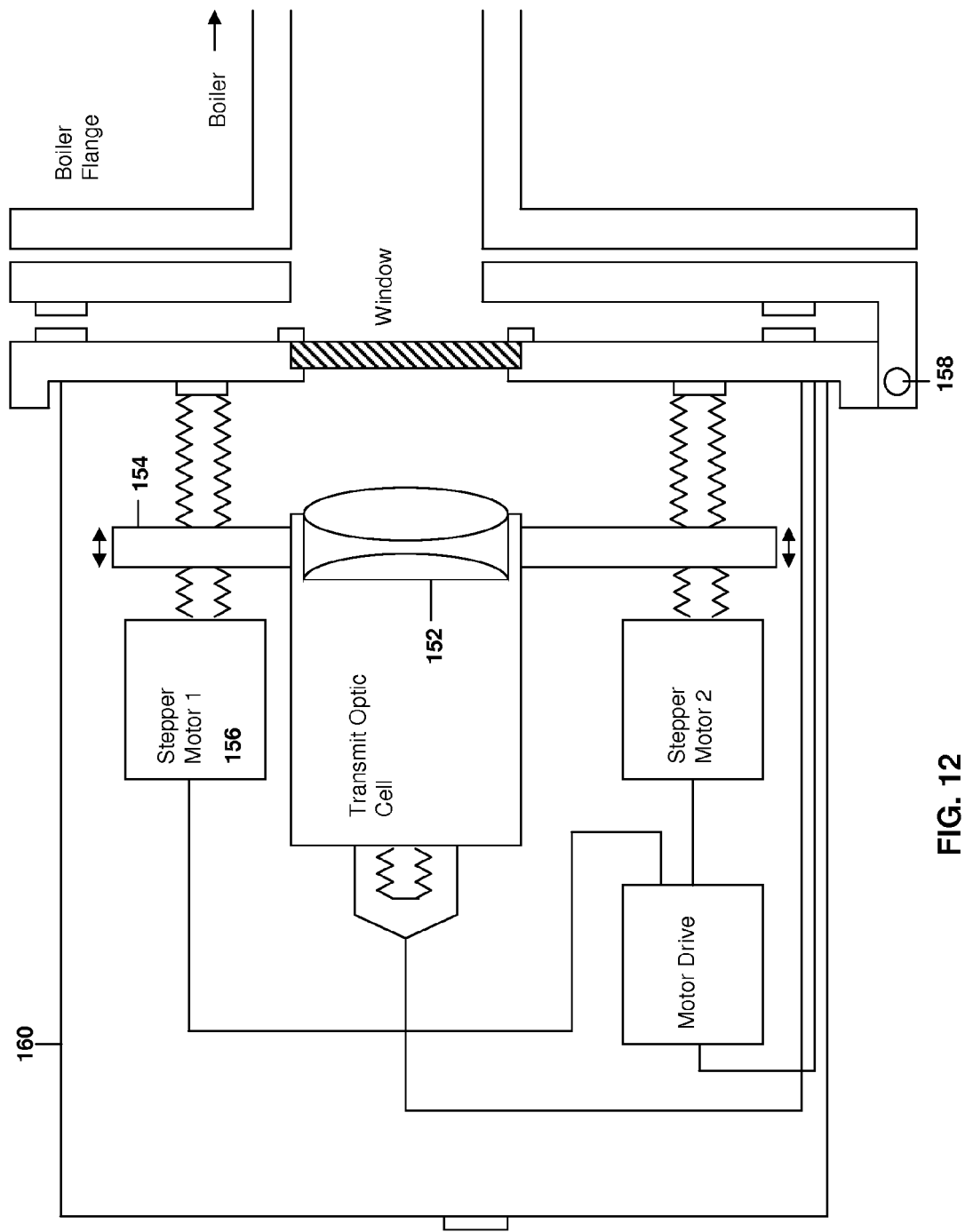
FIG. 12 is a schematic diagram of an alignment mechanism of the present invention.

FIG. 12 schematically illustrates an embodiment of alignable pitch or catch optics. The transmitter and receiver are similar in design: the transmitter generates a collimated beam of laser light from light emerging from an optical fiber, and the receiver captures a collimated beam of laser light and focuses it into a fiber. (It is possible to send light backward through this optical system, and most of the elements of the transmitter and receiver are identical.) The transmitter and receiver optics may be mounted in NEMA-4 enclosures to protect them from the environment. The following description applies to either the transmitter or receiver module.

As shown in FIG. 10, the pre-collimated fiber/lens pair 152 is attached to a kinematic tilt stage 154 positioned to allow tip and tilt perpendicular to the optical axis. Two direct-drive stepper motors 156 accomplish tip and tilt. These motors are controlled by computer via an Ethernet or similar connection. This connection may be through optical fiber in order to avoid electrical interference. The stepper motors 156 hold their position when power is removed, so the optical alignment is unaffected by electrical power outages.

During periodic or continuous system alignment, the control computer monitors the amount of laser light that is transmitted and detected. Preferably, a discrete alignment wavelength may be provided for continuous or periodic alignment proceedings such as the visible light source 64 of FIG. 3. Any misalignment will reduce this detected signal. In auto-alignment mode, the computer measures the detected signal, directs one of the two stepper motors to move a small amount in one direction, then re-measures the detected signal. If the signal increases, then the computer directs the stepper motor to move again in the same direction until the signal does not increase. The computer then directs the other stepper motor to move along the orthogonal axis to maximize the detected signal, then repeats the whole process for the other sensor head. As the detected signal increases, the detector amplifier gain automatically decreases so that the auto-alignment process proceeds over several decades of signal size. The auto-alignment system can function with detected powers from nanowatts to milliwatts.

This "hill-climbing" algorithm is able to align the system after near-total loss of signal, in the presence of substantial noise, and is tolerant of beam blockages, power outages, mechanical shocks and other disturbances that could cause other alignment systems to misalign to the limits of the control electronics. All that is required for auto-alignment is a finite signal with a global maximum in position space. Depending on specific installation conditions, auto-alignment may occur periodically at set intervals such as every hour or as needed after an extended period such as days of operation. The control computer may monitor the detected signal and auto-align only when the signal drops below a pre-set threshold.

The transmitter and receiver modules may incorporate several other features useful for industrial applications. Optional sensors may detect when the modules are moved out of position for cleaning or maintenance, and all lasers are turned off for safety. As shown on FIG. 10, all electrical and optical connections may made through a hinge 158 so that all such connections are undisturbed by maintenance operations. The enclosure 160 protects the sensitive internal optics from contaminants, and is preferable hosable. The hinge range of motion may be restricted to avoid operator injury. Preferably, each sensor head will require less than 10 watts of input electrical power during auto-alignment, and less than 0.1 watt after auto-alignment is complete.

Alternate designs may be suitable for different applications. Considerable size and weight reduction are possible if NEMA-4 enclosure rating is not required. Different transmission distances may allow optics of different focal length and clear aperture to optimize the captured signal. As an alternative to the stepper motor-driven tilt stage described above to control pointing by moving the entire fiber-lens assembly, the fiber may be moved laterally relative to the lens to effect the same pointing change while moving a much smaller mass. Different electromechanics such as piezoelectric elements or voice coils may also be used to increase the speed of the auto-alignment system.

In addition to the alignment concerns discussed above, the specific choice of pitch and catch optics can affect the performance of the TDLAS sensing system of the present invention in several ways:

(1) Signal strength coupled to the detectors depends on pitch/catch efficiency.

(2) The amount of undesirable background emission coupled to the detectors depends on catch optics etendue.

(3) The effects of few-mode noise at 760 nm are very sensitive to the pitch/catch configuration.

(4) The noise characteristics (small but more steady or larger with wild swings) are expected to depend on the launched beam size. A larger launch beam is preferable.

(5) The system misalignment sensitivity is a direct function of pitch and catch focal lengths and associated fiber sizes.

A very simplistic picture of a typical coal fired power plant combustion zone can be adopted for optical component selection analysis. The purpose of such analysis is to focus on the general effects on a laser beam passing through the fireball with as little knowledge of the fireball details as possible. Traversing the fireball has three effects on a light beam:

(1) Soot particles absorb some of the light.

(2) Large-angle refraction or scattering prevents some of the light from reaching the catch optic.

(3) Light passes through numerous small thermal gradients and is thus steered randomly but still reaches the catch optic.

Only the third category of light is available for collection. Assuming that a typical ray of light undergoes multiple refracting events while traversing the fireball, the direction of the ray follows a random path, and can drift away from its initial direction. If the ray is part of a larger beam composed of other rays that undergo similar but not identical drifts, then the effect of the fireball on the beam causes four distinct types of changes:

(1) Change in the overall direction of the entire beam (2) Change in the position of the centroid of the beam (3) Change in the beam size (4) Change in beam divergence/wavefront flatness These four types of changes are parameters which include all the major effects on the beam that will affect collection efficiency, without regard for the physics leading to these effects.

If the directions of the rays of light in the fireball are undergoing random drift then the ray directions may diffuse away from the initial (nominally optimum) direction according to a standard diffusion dependence. However, the distance of a ray of light from the original axis depends on its prior directions. Thus, for a given amount of rms beam steering, determined by the details of the fireball, a directly proportional amount of beam offset can be expected. If a laser beam traversing the fireball is blown up to several times its original size then the same relationship will hold between the final beam size and final beam divergence.

Light collection efficiency can be estimated if we know the angle, location and beam size of the light incident on the catch optics. The estimate assumes simple ray optics, flat-top intensities and a simple estimate the amount of light incident on the catch optic that is within the fiber numerical aperture NA and which is boresighted to strike the core of the fiber. The end result is a "hill" in offset-angle space. Assuming optimum alignment, collection efficiency is close to the top of the hill but may be rapidly moving over and around the hill as beam angle and position fluctuate. Preferably, the collection efficiency hill will be both as tall and as broad as possible. Several points about the hill are worth noting:

(1) The peak height of the collection efficiency hill (for zero beam offset and tilt) is proportional to the square of the catch optic etendue (focal length times NA) unless the catch optic is large enough to capture the entire incident beam, at which point the catch efficiency is 100%.

(2) The hill is elliptical, and changing the catch focal length makes one axis longer and the other shorter.

(3) The fluctuation in light collection efficiency due to beam jitter is a noise source.

Based upon the foregoing analysis techniques, the signal to noise ratio of different pitch/catch combinations may be compared. Assuming that the multiplicative noise is the same, different catch optics differ in final performance only if the fireball background noise or detector noise are dominant.

The objects of the invention have been fully realized through the embodiments disclosed herein. Those skilled in the art will appreciate that the various aspects of the invention may be achieved through different embodiments without departing from the essential function of the invention. The particular embodiments are illustrative and not meant to limit the scope of the invention as set forth in the following claims.

What is claimed is:

1. A method of sensing a process comprising:
providing laser light at multiple select lasing frequencies;
simultaneously multiplexing the select lasing frequencies of laser light;
transmitting the multiplexed laser light in a pitch side optical fiber to a pitch optic;
projecting the multiplexed laser light from the pitch optic through a process;
receiving the multiplexed laser light in a catch side optic;
transmitting the multiplexed laser light from the catch optic through a catch side optical fiber to a demultiplexer;
demultiplexing the multiplexed laser light;
transmitting a frequency of demultiplexed laser light to a detector; and
determining a combustion parameter from an output of the detector.

2. The method of sensing a process of claim 1 further comprising controlling the combustion process in accordance with the determined combustion parameter.

3. The method of sensing a process of claim of claim 1 further comprising:
optically coupling each of the more than one of the diode lasers to the multiplexer with an input optical fiber; and
optically coupling the output of the demultiplexer to the detector with an output optical fiber.

4. The method of sensing a process of claim 1 wherein the pitch side optical fiber is a single mode fiber.

5. The method of sensing a process of claim of claim 1 wherein the catch side optical fiber is a multimode fiber.

6. The method of sensing a process of claim of claim 1 further comprising:
routing the multiplexed laser light to more than one pitch optic with a pitch side optical routing device; and routing the multiplexed laser light to from more than one catch optic with a catch side optical routing device.

7. The method of sensing a process of claim 1 wherein one of the multiplexer and demultiplexer comprises an echelle grating.

8. The method of sensing a process of claim 7 wherein one of the multiplexer and demultiplexer further comprises:
- a multiplex optical waveguide propagating a plurality of optical channels of distinct wavelengths multiplexed as a single optical signal;
- a collimating/focusing optic optically coupled to the multiplex optical waveguide at a select focal length; and
- an echelle grating optically coupled to the collimating/focusing optic, the echelle grating comprising a groove spacing and a blaze angle providing for the simultaneous de/multiplexing of a plurality of ranges of wavelengths with each of the ranges of wavelengths being centered around a plurality of central wavelengths and with each of the central wavelengths corresponding to a select order of echelle grating operation.

9. The method of sensing a process of claim 8 wherein the plurality of optical channels of distinct wavelengths range from wavelengths equal to or greater than 670 nm to wavelengths equal to or less than 5200 nm.

10. The method of sensing a process of claim 8 wherein the select order of echelle grating operation is from $2^{nd}$ order to $14^{th}$ order.

11. The method of sensing a process of claim 8 wherein the groove spacing of the echelle grating is approximately 171.4 lines/mm and the blaze angle of the echelle grating is approximately 52.75 degrees.

12. The method of sensing a process of claim 1 further comprising:
- optically coupling the multiplexer to fewer than all of the diode lasers; and
- optically coupling multiplexed laser light from the pitch side optical fiber and un-multiplexed laser light from an un-multiplexed input optical fiber to the pitch optic with an optical coupler.

13. The method of sensing a process of claim 12 wherein the optical coupler optically communicates with the pitch optic through a select length of a transmitting optical fiber, and the length of the transmitting optical fiber is selected to maintain mode noise below a select level.

14. The method of sensing a process of claim 12 wherein a wavelength of the multiplexed laser light ranges from 1240 nm to 5200 nm and a wavelength of the un-multiplexed laser light is less than 1240 nm.

15. The method of sensing a process of claim 12 wherein the optical coupler optically communicates with the pitch optic through a select length of a transmitting optical fiber, the length of the transmitting optical fiber being selected such that the un-multiplexed laser light does not become multimodal during transmission through the transmitting optical fiber.

16. The method of sensing a process of claim 15 wherein the un-multiplexed input optical fiber is an SM 750 fiber and the pitch side optical fiber and the transmission optical fiber are SMF 28 optical fibers.

17. The method of sensing a process of claim 16 wherein the length of the transmission optical fiber is equal to or less than three meters.

18. The method of sensing a process of claim 1 further comprising mechanically manipulating a section of the catch side multimode optical fiber to minimize catch side mode noise.

19. The method of sensing a process of claim 1 further comprising actively aligning one of the pitch and the catch optic with respect to a direction of the projection of the multiplexed laser output to increase a quantity of laser light coupled to the catch side optical fiber.

\* \* \* \* \*